United States Patent [19]

Kalb

[11] Patent Number: 4,585,457
[45] Date of Patent: Apr. 29, 1986

[54] INFLATABLE INTRAOCULAR LENS

[76] Inventor: Irvin M. Kalb, 16 Peqout Trail, Westport, Conn. 06880

[21] Appl. No.: 734,539

[22] Filed: May 16, 1985

[51] Int. Cl.<sup>4</sup> ............................................. A61F 2/16
[52] U.S. Cl. ..................................................... 623/6
[58] Field of Search ....................................... 623/6–8, 623/11

[56] References Cited

U.S. PATENT DOCUMENTS

| 3,934,274 | 1/1976 | Hartley, Jr. | 623/8 |
| 4,249,272 | 2/1981 | Poler | 623/6 |
| 4,253,199 | 3/1981 | Banko | 623/6 |
| 4,373,218 | 2/1983 | Schachar | 623/6 |

OTHER PUBLICATIONS

"Refilling the Rabbit Lens" by J. Kessler, Arch. Optthal, vol. 76, Oct. 1966, pp. 596–598.

*Primary Examiner*—Ronald L. Frinks
*Attorney, Agent, or Firm*—David N. Koffsky

[57] ABSTRACT

An intraocular lens for use as an artificial lens implant is disclosed wherein the lens material is flexible and fluid impervious. Valve means communicate with the lens and enable it to be inflated with an appropriate fluid once the lens is placed in the eye.

6 Claims, 4 Drawing Figures

INFLATABLE INTRAOCULAR LENS

BACKGROUND OF THE INVENTION

This invention relates to intraocular lenses and, more particularly to a lens which employs a fluid as its primary lens medium.

Intraocular lenses generally consist of a medial lens body and a plurality of lateral lobes or position fixing elements (haptics) projecting from the circumference of the lens body for fixing the lens in the eye. The insertion of such a lens in the eye requires the surgeon to make a corneo-scleral incision sufficiently long to not only accommodate the passage of the lens, but also the position fixing haptics. Historically, the length of such an incision has approximated 6 to 9 mm.

Efforts have been made, and continue to be made to reduce the length of the required incision by redesign of the lens structure. In my copending patent application, entitled "Intraocular Lens with Retractable Legs", Ser. No. 649,798, I describe an intraocular lens wherein the positioning haptics are held in a retracted position until the lens is inserted in the eye, at which time the surgeon releases the haptics which automatically act to properly position the lens. Such a lens structure enables the surgeon to emplace with ease, the lens in the capsular bag and assures the least traumatic effect on the patient.

Other intraocular lenses of different design, but whose purpose is to reduce the dimension of the surgeon's incision, are shown in U.S. Pat. Nos. 4,296,501 and 4,343,050 to Charles Kelman.

All of the above-mentioned lenses are "solid" in that their minimum size is determined by the size of the lens element, notwithstanding what is done to the lens' positioning elements. In U.S. Pat. No. 4,466,705 of Paul Michelson, an intraocular capsular lens is described whose lens medium is a liquid material. Michelson's capsule is constructed of a semipermeable transparent membrane which is inserted in a dehydrated state into the eye. The capsule then hydrates and expands to a lens-like shape. Since the lens is inserted in a dehydrated state, Michelson suggests that it can be inserted through a small incision by folding or rolling it into a compact form. While this design does substantially reduce the size of the required incision (to 3 or 4 mm), the final lens configuration is difficult to control. In addition, there is no way to correct for any malformation of the lens once it is in place, if for any reason, the lens does not hydrate in accordance with expectations.

Recently, it has been reported that cataracts may be removed by phacoemulsification through a one millimeter non-sutured incision (ie. see Shearing, et al. pp. 6-11, CATARACT January 1985). Unfortunately there has been no intraocular lens which could be inserted through such a small incision.

OBJECTS OF THE INVENTION

It is an object of the invention to provide an intraocular lens whose insertion into the eye may be accomplished through a minimal incision.

A further object of the invention is to provide an intraocular lens whose characteristics are adjustable after insertion.

SUMMARY OF THE INVENTION

In accordance with the aforementioned objects, an intraocular lens has been developed which comprises impermeable, anterior and posterior transparent sheets joined to make a lens cavity. Appropriate haptics depend from the periphery of the lens cavity. A valve structure communicates with the lens cavity and is employed to fill the cavity with a suitable fluid of the proper index of refraction. Prior to insertion, and in its unfilled state, the lens cavity is folded and/or rolled and inserted into a probe of minimal diameter. The probe is then introduced through a corneal incision, the lens is pushed from the probe, expands and a syringe attached to the valve structure fills the lens with the proper amount of fluid to create the desired lens optic.

DESCRIPTION OF PREFERRED EMBODIMENT

Figure 1:
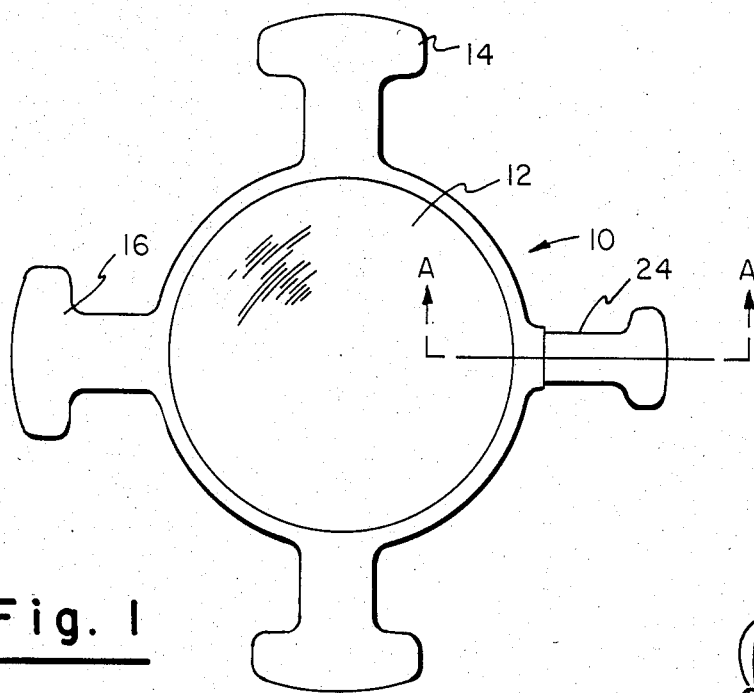
FIG. 1 is a plan view of an intraocular lens in accordance with the invention.

Referring now to FIG. 1, intraocular lens 10 consists of two distinct parts, an optic 12 and two or more haptics 14, 16, etc. Optic 12 comprises two sheets 20 and 22 (See FIG. 2) of an optically transparent, somewhat flexible polymer which is biocompatible. Sheets 20 and 22 are joined around their periphery to form fluid tight capsule. Joined to the periphery of lens 1 are a plurality of haptics, at least one of which, 24 is hollow and communicates with the interior of optic 12.

Figure 2:
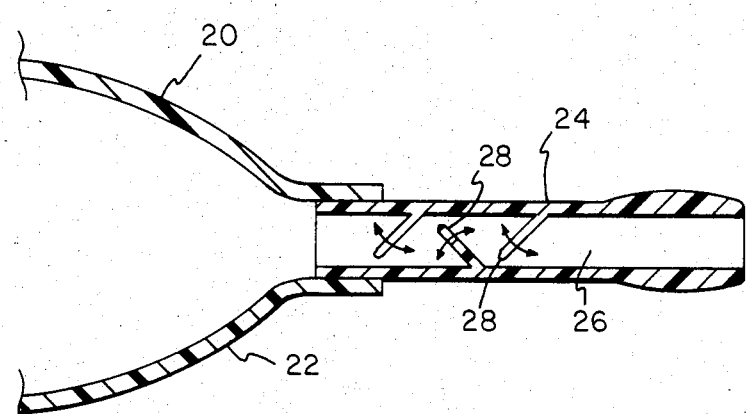
FIG. 2 is a cross sectional view along line A—A in FIG. 1.
Figure 4:
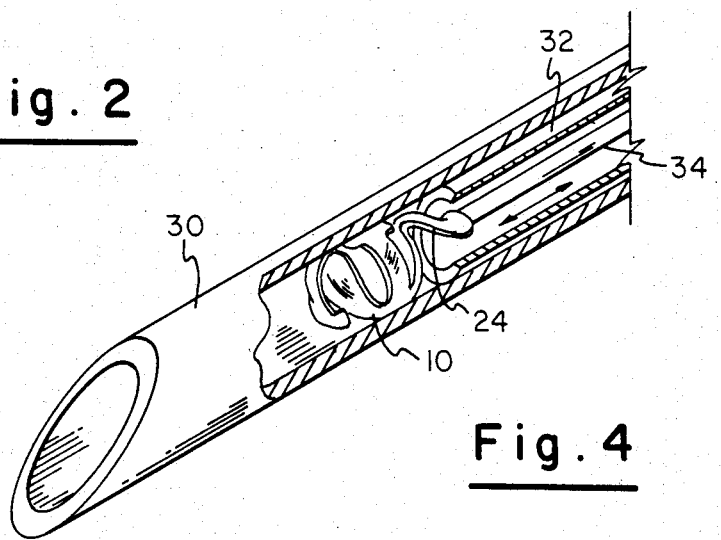
FIG. 4 is a perspective view of the lens inserter probe.

Haptic 24 is shown in greater detail in FIG. 2 and includes a lumen 26. Within lumen 26 are a plurality of shutters 28 which act as a one-way valve through which a fluid can be injected into the interior of optic 12. It should be clear to one skilled in the art that any suitable one way valve can be utilized, either integral to a haptic or communicating directly with the optic 12.

Figure 3:
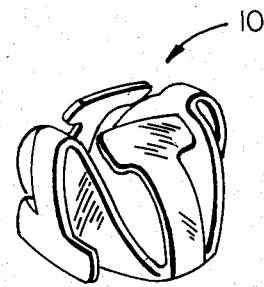
FIG. 3 is an end view of the intraocular lens in its folded state.

Prior to use, optic 12 is "deflated" in that sheets 20 and 22 are collapsed upon one another. In such a condition (See FIG. 3) intraocular lens 10 may be folded accordion style, rolled or otherwise reduced in size to enable it to be inserted into the lumen of inserting probe 30. A slideably mounted tube 32 is positioned within probe 30 so as to be able to be operated to push lens 10 into position once probe 30 has been inserted by the surgeon into the eye. Connected to lumen 26 of haptic 24 is an extended needle 34 which is attached to a precision syringe (not shown).

Upon insertion of lens 10 into place, the surgeon injects a biocompatible fluid of proper refractive index through needle 34, lumen 26, valve leaflets 28 into the area between sheets 20 and 22. The amount of injected fluid is precisely metered to achieve the proper lens configuration. Ordinarily, the lens, once inflated, assumes a bioconvex shape but by proper selection of materials, it can be made plano-convex, or concavo-convex.

The fluid, once inserted, does not escape due to the back pressure exerted upon leaflets 28 which causes them to seal lumen 26 to outward fluid flow. After inflation, needle 34 is removed by a twisting withdrawal motion from haptic 24. Then probe 30 is withdrawn, haptic 24 properly positioned and the wound closed.

Preferably, the haptics and optic are made of the same material. Any material is suitable which is biocompatible, transparent and has sufficient flexibility and strength to withstand the pressure exerted by inflation. Materials such as Polymethyl methacrylete (PMMA), polycarbonate and silicone elastoms, are among those which are acceptable. Typically sheets 20 and 22 will have a thickness of 30 to 50 microns and the lens diameter will approximate 6.2 to 8.2 mm. Under such conditions lens 10 can be folded sufficiently small to fit into a probe of less than 1.2 to 3.4 mm outer diameter. The inflating fluid must be bubble free, sterile, optically clear, biocompatible and have the proper index of refraction. Suitable inflating fluids are solutions of physiologic salts (index 1.33 to 1.44) and Dextran (index 1.39 to 1.4). The inflating fluid may also be a polymeric material such as a Silastic.

The intraocular lens of this invention may be shaped (by varying the dimension of the haptics) to fit into the eye's anterior chamber, posterior chamber and/or the capsular bag. Furthermore, the lens is susceptible to adjustment when in-place by step-wise additions of discrete amounts of injected fluid until the proper correction is achieved.

It will be understood that the above description of the invention is susceptible to various modifications, changes and adaptations and the same are intended to be comprehended with in meaning and range of equivalents of the appended claims.

I claim:

1. An intraocular lens comprising:
    a pair of flexible, optically transparent, fluid impervious sheet members joined to form a lens capsule;
    flexible positioning member means depending from said capsule, sized to be contained totally within the eye when in the extended position, and adapted to position the capsule once it is emplaced within the eye; and
    valve means integral with a positioning member means and communicating with the interior of said lens capsule and adapted to pass and retain a fluid into said lens capsule to thereby enable inflation of said capsule into the desired lens shape once it is emplaced within the eye.

2. The invention as defined in claim 1 wherein said valve means comprises a lumen, one end of which communicates with said capsule, the other end of which is adapted to removably mate with filling means, said valve means further including, intermediate thereof, a one-way valve which only allows fluid flow from said filling means into said lens capsule.

3. The invention as defined in claim 2 wherein said sheet members and positioning members are sufficiently flexible to allow said intraocular lens to be compressed in size by folding or rolling and inserted into an insertion probe.

4. The invention as defined in claim 3 wherein said fluid has an index of refraction greater than one.

5. The invention as defined in claim 4 wherein said fluid comprises a polymeric material of gel-like consistency.

6. The invention is defined in claim 2 wherein said one way valve includes a movable member within said lumen, which member seals said lumen in response to pressure exerted by fluid within said lens capsule.

* * * * *